US00PP30410P2

(12) United States Plant Patent
Holtmaat

(10) Patent No.: US PP30,410 P2
(45) Date of Patent: Apr. 16, 2019

(54) ***ECHINACEA* PLANT NAMED 'ECH391'**

(50) Latin Name: *Echinacea purpurea*
Varietal Denomination: ECH391

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 15/732,939

(22) Filed: Jan. 12, 2018

(51) Int. Cl.
*A01H 5/02* (2018.01)

(52) U.S. Cl.
USPC ..... Plt./428

(58) Field of Classification Search
USPC ..... Plt./428
CPC . A01H 5/025; A01H 5/02; A01H 5/00; A01H 6/14; A01H 6/1448
See application file for complete search history.

*Primary Examiner* — June Hwu
(74) *Attorney, Agent, or Firm* — C. A. Whealy

(57) ABSTRACT

A new and distinct cultivar of *Echinacea* plant named 'ECH391', characterized by its upright plant habit; moderately vigorous growth habit; freely branching habit; strong flowering stems; numerous large single-type inflorescences with pale yellow-colored ray florets that are red purple towards the base and dark purple-colored receptacle spines; and good garden performance.

2 Drawing Sheets

Botanical designation: *Echinacea purpurea.*
Cultivar denomination: 'ECH391'.

BACKGROUND OF THE INVENTION

The present invention relates to a new and distinct cultivar of *Echinacea* plant, botanically known as *Echinacea purpurea*, and hereinafter referred to by the name 'ECH391'.

The new *Echinacea* plant is a product of a planned breeding program conducted by the Inventor in Zuidwolde, The Netherlands. The objective of the breeding program is to develop new freely branching and relatively compact *Echinacea* plants with unique and attractive ray floret coloration.

The new *Echinacea* plant originated from a cross-pollination made by the Inventor in July, 2014 in Zuidwolde, The Netherlands of two unnamed seedling selections of *Echinacea purpurea*, not patented. The new *Echinacea* plant was discovered and selected by the Inventor as a single flowering plant within the progeny of the stated cross-pollination in a controlled greenhouse environment in Zuidwolde, The Netherlands in July, 2016.

Asexual reproduction of the new *Echinacea* plant by in vitro meristem culture in a controlled environment in Zuidwolde, The Netherlands since March, 2017 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'ECH391'. These characteristics in combination distinguish 'ECH391' as a new and distinct *Echinacea* plant:

1. Upright plant habit.
2. Moderately vigorous growth habit.
3. Freely branching habit.
4. Strong flowering stems.
5. Numerous large single-type inflorescences with pale yellow-colored ray florets that are red purple towards the base and dark purple-colored receptacle spines.
6. Good garden performance.

Plants of the new *Echinacea* can be compared to plants of the parent selections. Plants of the new *Echinacea* differ primarily from plants of the parent selections in growth habit as plants of the new *Echinacea* are more compact and uniform than plants of the parent selections.

Plants of the new *Echinacea* can be compared to plants of *Echinacea purpurea* 'Mistral', disclosed in U.S. Plant Pat. No. 20,498. In side-by-side comparisons, plants of the new *Echinacea* differ primarily from plants of 'Mistral' in the following characteristics:

1. Plants of the new *Echinacea* are taller than plants of 'Mistral'.
2. Plants of the new *Echinacea* and 'Mistral' differ in ray floret color as plants of 'Mistral' have red purple-colored ray florets.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet is a side perspective view of a typical flowering plant of 'ECH391' grown in a container.

The photographs on the second sheet are close-up views of typical inflorescences (upper photograph) and typical leaves (lower photograph) of 'ECH391'.

DETAILED BOTANICAL DESCRIPTION

The aforementioned photographs and following observations and measurements describe plants grown during the summer in 21-cm containers in an outdoor nursery in Zuidwolde, The Netherlands and under cultural practices typically used in commercial *Echinacea* production. During the production of the plants, day temperatures ranged from 18° C. to 32° C. and night temperatures ranged from 8° C. to 20° C. Plants were six months old when the photographs and description were taken. In the following description, color references are made to The Royal Horticultural Society Colour Chart, 2015 Edition, except where general terms of ordinary dictionary significance are used.

Botanical classification: *Echinacea purpurea* 'ECH391'.

Parentage:

*Female, or seed, parent*.—Unnamed seedling selection of *Echinacea purpurea*, not patented.

*Male, or pollen, parent*.—Unnamed seedling selection of *Echinacea purpurea*, not patented.

Propagation:

*Type*.—By in vitro meristem culture.

*Time to initiate roots, summer*.—About 15 days at temperatures about 25° C.

*Time to produce a rooted young plant, summer*.—About five weeks at temperatures about 21° C.

*Root description*.—Fine, fibrous; typically pale cream in color, actual color of the roots is dependent on substrate composition, water quality, fertilizer type and formulation, substrate temperature and physiological age of roots.

*Rooting habit*.—Freely branching; dense.

Plant description:

*Plant form and growth habit*.—Herbaceous perennial; upright plant habit, roughly ovate in overall shape; freely branching habit with about 14 lateral branches developing per plant; moderately vigorous growth habit; low to moderate growth rate.

*Plant height*.—About 35.8 cm.

*Plant diameter or spread*.—About 34 cm.

*Lateral branches*.—Length: About 14.5 cm. Diameter: About 4 mm. Internode length: About 1.7 cm. Aspect: About 10° from vertical. Strength: Strong. Texture: Moderately pubescent, rough. Color: Close to 144B.

Leaf description:

*Basal leaves*.—Arrangement: Alternate, simple. Length: About 10.3 cm. Width: About 2.7 cm. Shape: Narrowly ovate to lanceolate; slightly carinate. Apex: Acute. Base: Attenuate. Margin: Shallowly dentate; undulate. Texture and luster, upper and lower surfaces: Moderately pubescent, strigose, rough; matte. Venation pattern: Pinnate. Color: Developing leaves, upper surface: Close to 143A. Developing leaves, lower surface: Close to 146B. Fully expanded leaves, upper surface: Close to NN137B; venation, close to 144A to 144B. Fully expanded leaves, lower surface: Close to 137C; venation, close to 146D. Petioles, basal leaves: Length: About 7.6 cm. Width: About 2 mm. Height: About 2 mm. Strength: Strong, flexible. Texture, upper surface: Smooth, glabrous. Texture, lower surface: Sparsely pubescent. Color, upper surface: Close to 144A; margins, close to 143A. Color, lower surface: Close to 146D; margins, close to 143A.

*Cauline leaves*.—Arrangement: Alternate, simple. Length: About 11 cm. Width: About 2.2 cm. Shape: Narrowly ovate to lanceolate; slightly carinate. Apex: Acute. Base: Attenuate. Margin: Shallowly dentate; undulate. Texture and luster, upper and lower surfaces: Moderately pubescent, strigose, rough; matte. Venation pattern: Pinnate. Color: Developing leaves, upper surface: Close to 143A. Developing leaves, lower surface: Close to 146B. Fully expanded leaves, upper surface: Close to NN137B; venation, close to 144A to 144B. Fully expanded leaves, lower surface: Close to 137C; venation, close to 146D. Petioles, cauline leaves: Length: About 2 cm. Width: About 2 mm. Height: About 2 mm. Strength: Strong, flexible. Texture, upper surface: Smooth, glabrous. Texture, lower surface: Sparsely pubescent. Color, upper surface: Close to 144A; margins, close to 143A. Color, lower surface: Close to 146D; margins, close to 143A.

Inflorescence description:

*Appearance*.—Large single-type inflorescences with ray and disc florets arranged on a capitulum; inflorescences positioned upright above the foliar plane on strong peduncles.

*Flowering habit*.—Freely flowering habit with about 45 inflorescences developing per plant during the flowering season.

*Fragrance*.—None detected.

*Time to flower*.—Plants flower continuously from early July to late September in the garden in The Netherlands.

*Inflorescence longevity*.—Inflorescences maintain good substance for about two to three weeks on the plant; inflorescences persistent.

*Inflorescence buds*.—Height: About 2.7 cm. Diameter: About 3 cm. Shape: Flattened globular. Texture: Smooth, glabrous Color: Darker than 166A; developing ray florets, close to 4D tinged towards the base with close to 51C.

*Inflorescence size*.—Diameter: About 11.3 cm. Depth (height): About 4.7 cm. Disc diameter: About 3 cm.

*Receptacles*.—Height: About 1.2 cm. Diameter: About 8 mm. Color: Close to 157D.

*Ray florets*.—Quantity and arrangement: About 16 arranged in a single whorl. Length: About 5 cm. Width: About 1.1 cm. Shape: Oblanceolate. Apex: Praemorse. Base: Cuneate. Margin: Entire. Texture and luster, upper surface: Smooth, glabrous, carinate; matte. Texture and luster, lower surface: Smooth, glabrous, carinate; slightly glossy. Aspect: Slightly upright, about 30° above horizontal. Color: When opening, upper surface: Close to 4D; towards the apex, close to 4C to 4B; base, tinged with close to 54C. When opening, lower surface: Close to 4D; base, tinged with close to 51C. Fully opened, upper surface: Close to 4D to slightly lighter than 4D; towards the apex, close to 4C; base, strongly tinged with close to 64D; with development, color becoming closer to 158A to 158B and at the base, tinged with close to 54C. Fully opened, lower surface: Close to 4D to slightly lighter than 4D; towards the apex, close to 2D to 2C; base, strongly tinged with close to 64D; with development, color becoming closer to 158A to 158B and at the base, tinged with close to 54C.

*Disc florets*.—Quantity and arrangement: About 180 per inflorescence, arranged spirally at the center of the receptacle. Length: About 1 cm. Diameter: About 2 mm. Shape: Tubular; proximally, 10% free, not fused. Apex: Acute. Base: Fused. Margin: Entire. Aspect: Mostly upright. Texture and luster, inner and outer surfaces: Smooth, glabrous; glossy. Color, when opening, inner and outer surfaces: Apex: Close to 183D. Mid-section and base: Close to N148D. Color, fully opened, inner and outer surfaces: Apex: Close to 147C tinged with close to 183D. Mid-section and base: Close to N148D.

*Receptacle spines*.—Quantity: One per disc floret. Length: About 1 cm. Diameter: About 1 mm. Shape: Acicular. Apex: Acute. Base: Attenuate. Texture and luster: Smooth, glabrous; glossy. Color: Apex: Close to N186C. Mid-section: Close to 24B. Base: Close to 145C.

*Involucral bracts*.—Quantity per inflorescence: About 50 arranged in about three whorls. Length: About 9 mm. Width: About 2 mm. Shape: Ovate to narrowly ovate. Apex: Acute. Base: Cuneate. Margin: Entire; moderately pubescent. Texture, upper surface: Smooth, glabrous. Texture, lower surface: Moderately pubescent. Color, upper surface: Close to 137C; base, close to 138C. Color, lower surface: Close to 138B.

*Peduncles*.—Length, terminal peduncle: About 13.5 cm. Length, fourth peduncle: About 10 cm. Diameter, terminal peduncle: About 3 mm. Strength: Strong. Aspect, terminal peduncle: Upright. Aspect, secondary peduncles: About 20° from vertical. Texture: Moderately pubescent. Color: Close to 144A.

*Reproductive organs*.—Androecium (present only on disc florets): Quantity per floret: Five. Filament length: About 3 mm. Filament color: Close to 151D. Anther length: About 2 mm. Anther shape: Lanceolate. Anther color: Close to N199A. Pollen amount: Moderate. Pollen color: Close to 14B. Gynoecium (present only on disc florets): Quantity per floret: One. Pistil length: About 6 mm. Style length: About 4.5 mm. Style color: Close to 145B. Stigma shape: Decurrent, unequal. Stigma color: Close to 203A. Ovary color: Close to 145D. Seeds and fruits: Seed and fruit development have not been observed on plants of the new *Echinacea* to date.

Pathogen & pest resistance: Plants of the new *Echinacea* have not been shown to be resistant to pathogens and pests common to *Echinacea* plants to date.

Garden performance: Plants of the new *Echinacea* have exhibited good garden performance and to tolerate rain and wind. Plants of the new *Echinacea* have been observed to tolerate high temperatures of about 35° C. and to be suitable for USDA Hardiness Zones 3 to 10.

It is claimed:

1. A new and distinct *Echinacea* plant named 'ECH391' as illustrated and described.

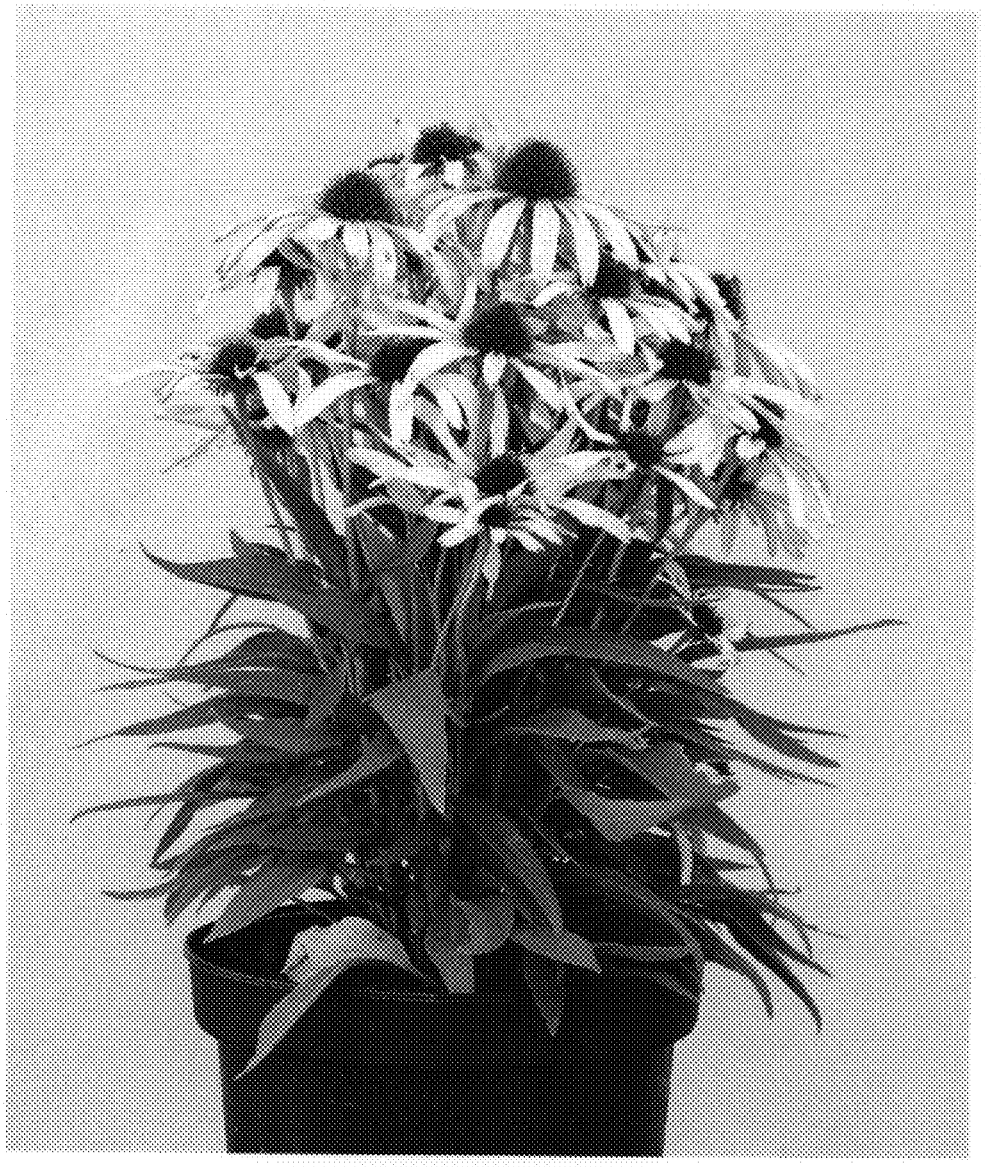

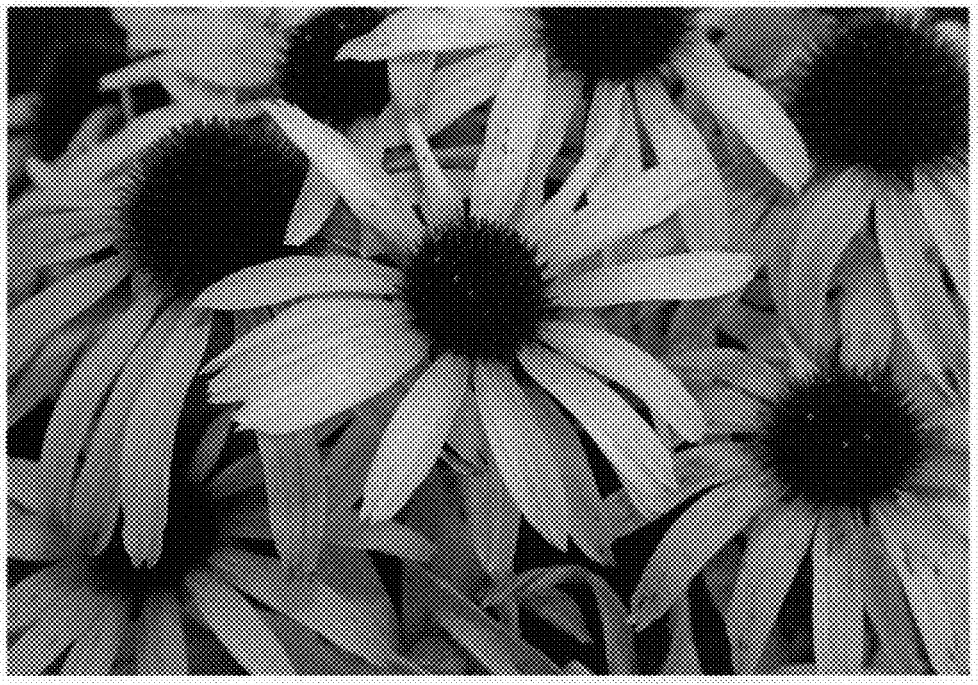
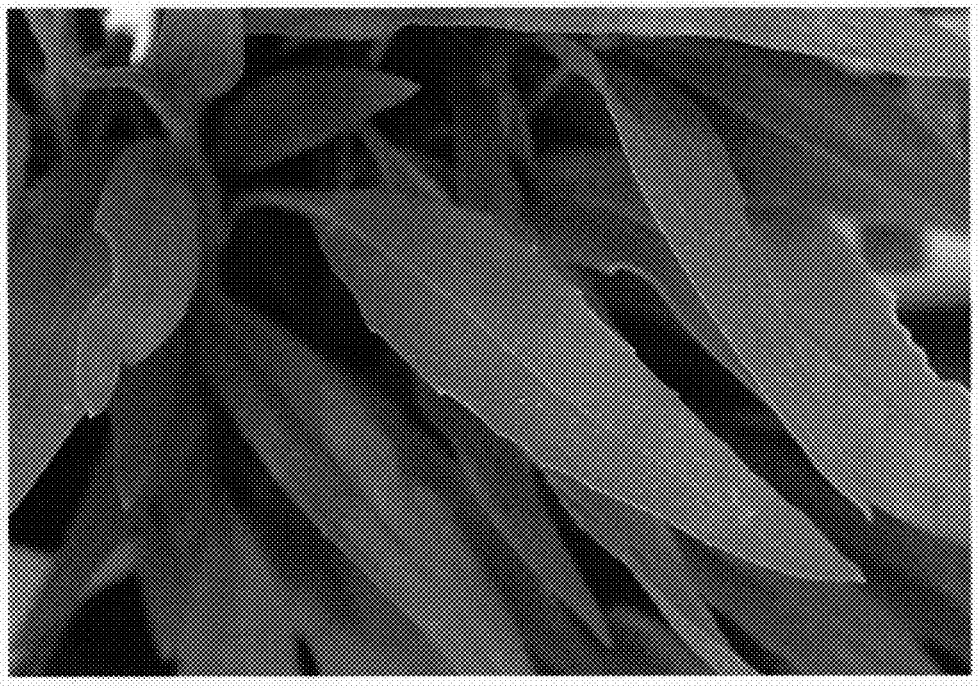

* * * * *